Figure 1:
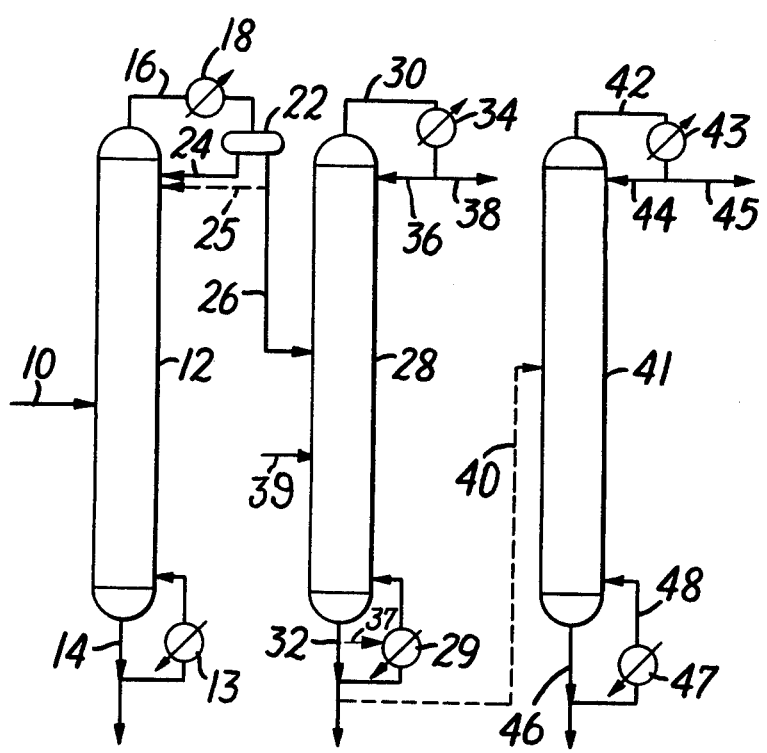

United States Patent [19]

Becker et al.

[11] 4,028,195

[45] June 7, 1977

[54] RECOVERY OF ALKYLENE GLYCOLS BY DISTILLATION WITH AQUEOUS ORGANIC ACID

[75] Inventors: Mitchell Becker, Teaneck; Charles C. Yang, Hackensack, both of N.J.

[73] Assignee: Halcon International, Inc., New York, N.Y.

[22] Filed: Sept. 12, 1975

[21] Appl. No.: 612,827

[52] U.S. Cl. .................................. 203/38; 203/53; 203/60; 203/95; 260/637 R
[51] Int. Cl.² ..................... B01D 3/34; C07C 29/26
[58] Field of Search ............ 203/38, 53, 61, 95–97, 203/6; 260/637 R

[56] References Cited

UNITED STATES PATENTS

| | | | |
|---|---|---|---|
| 3,398,061 | 8/1968 | Taul | 260/637 R |
| 3,408,268 | 10/1968 | Pitts et al. | 260/637 R |
| 3,647,892 | 5/1972 | Hoch | 260/637 R |
| 3,809,724 | 5/1974 | Golden | 260/637 R |

Primary Examiner—Wilbur L. Bascomb, Jr.
Attorney, Agent, or Firm—William C. Long; David Dick; Riggs T. Stewart

[57] ABSTRACT

Ethylene glycol or 1,2-propylene glycol contained in mixtures with lower carboxylate esters of the glycol are separated from such mixtures by fractional distillation of the mixtures with the addition to the lower portion of the distillation zone of aqueous formic acid and/or acetic acid.

5 Claims, 2 Drawing Figures

RECOVERY OF ALKYLENE GLYCOLS BY DISTILLATION WITH AQUEOUS ORGANIC ACID

This invention relates to the separation of ethylene glycol or 1,2-propylene glycol from mixtures containing the glycol in admixture with small amounts of lower carboxylate esters of the glycol, particularly the ethylene or propylene glycol monocarboxylate and/or the ethylene or propylene glycol dicarboxylate.

Ethylene glycol and 1,2-propylene glycol (hereafter referred to as propylene glycol) are chemicals of acknowledged commercial importance. Ethylene glycol is used, for example, in the preparation of anti-freeze compositions and in the manufacture of polyester fibers. Ethylene glycol manufacturing processes of commercial interest have generally been based upon ethylene oxide as a raw material. Recently, however, processes have been developed which make it possible to produce ethylene glycol and propylene glycol without the necessity for the intermediate manufacture of the oxide. These processes employ the liquid-phase reaction of the olefin, a carboxylic acid and molecular oxygen in the presence of a catalyst to produce carboxylic acid esters of ethylene or propylene glycol. A process of this type is disclosed in Belgian Patent No. 738,104. The glycol can be liberated by hydrolysis of the carboxylate esters produced in these processes. The conversion of the esters to the glycol is limited by equilibria and the recovery and separation of the glycol produced in the hydrolysis reaction from the unconverted carboxylate esters involves many difficulties because of the formation of glycol-carboxylate ester azeotropes. However, separation of the glycol from the glycol esters by azeotropic distillation is disclosed in Golden U.S. Pat. No. 3,809,724, the disclosure of which is incorporated herein by reference. In the process of that patent, the overhead distillate glycol product still contains small amounts of glycol esters, particularly the monoester, and azeotropic agent, and these contaminants are separated from the glycol by fractional distillation. During this distillation, the contaminants are removed as distillate and the purified ethylene glycol is recovered as a bottom product. It has been observed, however, that the monoester tends, at least in part, to be converted in the environment of the distillation zone to the corresponding glycol ortho ester. The ortho ester is higher boiling than the simple ester and tends to move downwardly in the distillation zone. In the lower part of the distillation zone, however, it decomposes and reverts to the simple ester which thus contaminates the product glycol in the bottoms and intefers with a fully effective separation of the glycol monoester from the glycol, the preferred objective of the distillation.

It is an object of this invention to provide a process for the effective recovery of ethylene glycol or propylene glycol from mixtures of the glycol with lower carboxylate esters of the glycol.

It is an additional object of this invention to provide a process for the effective recovery of ethylene or propylene glycol produced by the hydrolysis of lower carboxylate esters of the glycol.

It is a further object of the invention to provide a process for the separation of ethylene or propylene glycol from reaction mixtures produced by the hydrolysis of lower carboxylate esters of the glycol.

Other objects of the invention will be apparent from the following description of the invention and of illustrative embodiments thereof.

The following description is presented with reference to ethylene glycol, it being understood that the description is equally and fully applicable to propylene glycol.

In accordance with the invention, contaminants in ethylene glycol, especially ester contaminants such as lower carboxylate monoesters of ethylene glycol, e.g., ethylene glycol monoacetate and ethylene glycol monoformate, are removed from the ethylene glycol by fractionally distilling the contaminated ethylene glycol in a distillation zone into the lower portion of which is introduced aqueous formic acid and/or aqueous acetic acid. It has been surprisingly discovered that when aqueous formic acid and/or aqueous acetic acid is present in the lower portion of the distillation zone, the formation of the above-mentioned ortho ester is prevented so that the monoester to be separated is not converted into a higher boiling form and the free monoester can accordingly be fractionally distilled away from the ethylene glycol. Only relatively small amounts of the aqueous formic acid and/or acetic acid are required to bring about this surprising and desirable result. Thus, in general, 0.5 to 10% of water, 0.02 to 2.50% of formic acid and/or 0.02 to 5% of acetic acid, based on the weight of the feed, are introduced into the distillation zone. The acids and water may be separately introduced, i.e., as separate streams but, preferably, they are fed together as an aqueous mixture or solution. These additives are introduced into the distillation zone at a point below the point of introduction of the feed being subjected to distillation.

In a typical continuous distillation of contaminated ethylene glycol, the ethylene glycol is fed into the central portion of the distillation zone, i.e., in an area ranging approximately between the bottom third and the upper fourth of the distillation zone, which is typically a fractional distillation column having an appropriate number of plates to effect the desired separation. The aqueous formic acid and acetic acid additive is thus introduced into the distillation zone at a point below the point at which the contaminated ethylene glycol is fed into the zone. Preferably, the aqueous formic acid and/or acetic acid additive is fed into the lower fourth of the distillation zone, but the exact point of introduction is not critical as long as it is below the feed point.

In accordance with a preferred embodiment, a small amount of water is also added to the pot or reboiler. Typically, the amount of this additional water is 0.2 to 5%, preferably 0.5 to 1.5% by weight of the feed to the column. Alternatively, but less preferably, this additional water may be added at a point close to the reboiler, rather than in the reboiler itself, i.e., at a point below the point of addition of the aqueous acetic acid or formic acid, but closer to the reboiler than to the point of acid addition.

Although the process of the invention is applicable to the purification of ethylene glycol containing lower carboxylate monoesters derived from any source, from a practical standpoint the content of monoesters is generally an amount up to about 65 mol % and the process of the invention is particularly adapted to the treatment of the glycol phase obtained by the azeotropic distillation of glycol admixed with substantial amounts of lower carboxylate monoesters and lower carboxylate diesters such as are obtained by the hydrolysis of lower carboxylate esters of the glycol. The invention will thus be advantageously described by reference to a feed derived from such sources.

Thus, to provide a feed to the distillation process of the present invention ethylene glycol is separated from mixtures thereof with substantial amounts of lower carboxylate esters of ethylene glycol, such as mixtures produced by the hydrolysis of lower carboxylate esters of ethylene glycol, by distilling such mixtures in the presence of an azeotroping agent which is essentially waterimmiscible and which forms a minimum-boiling azeotrope with ethylene glycol and which preferably has a boiling point at atmospheric pressure of 135° to 220° C, most preferably 150° to 200° C. When the ethylene glycol-containing mixture is distilled in the presence of such azeotroping agents, the distillate separates into two phases, viz., a phase composed essentially of the azeotroping agent and a phase containing the ethylene glycol. The phase containing the azeotroping agent is readily separated, as by decantation, from the ethylene glycol-containing phase and is returned to the distillation column as reflux. Consequently, the azeotroping agent is merely recirculated in the distillation system and the originally-supplied quantity of azeotroping agent is continually available for reuse except for the very small normally-encountered handling losses. Preferably, as disclosed in the application of Chun Fei Chueh, being filed on even date herewith, and identified as Case 1088, the disclosure of which application is incorporated herein by reference, a controlled quantity of the glycol-containing phase is also returned to the distillation column as reflux. The reflux ratio of the glycol-containing phase is typically at least 0.3:1, preferably at least 0.5:1 and most preferably at least 1:1. From a practical standpoint, the reflux ratio of the glycol-containing phase is generally not above 8:1 although it can be higher if desired. Preferably, all of the phase containing the azeotroping agent is returned to the distillation column as reflux. When both the azeotroping agent and the product glycol are refluxed to the distillation zone in this mmaner there is a significant improvement in the purity of the glycol removed as distillate.

Suitably, the azeotroping agent has a boiling point within the above-indicated 135° to 220° C range at atmospheric pressure, most advantageously within the specified preferred temperature range. Particularly suitable as azeotroping agents are the saturated hydrocarbons, both acyclic and cyclic, the aromatic hydrocarbons, which are for the most part, alkyl-substituted benzenes, and the halogenated hydrocarbons, especially halogenated aromatic hydrocarbons. Especially preferred azeotroping agents are the tri-methyl benzenes, particularly 1,2,3-trimethylbenzene. Azeotroping agents also include ethers, ketones and alcohols. Table A below identifies examples of azeotroping agents of this character and indicates the boiling point of the azeotrope with ethylene glycol.

TABLE A

| Azeotroping Agent | Azeotrope b.p., ° C 760 mm.Hg | Agent b.p., ° C 760 mm.Hg |
|---|---|---|
| Ethylbenzene | 133 | 136.2 |
| Cumene | 147 | 152.8 |
| Anisole | 150.5 | 153.9 |
| Bromobenzene | 150.2 | 156 |
| 1-Bromohexane | 150.5 | 156 |
| 1,2,3-Trichloropropane | 150.8 | 156.9 |
| Propybenzene | 152 | 159 |
| o-Chlorotoluene | 152.5 | 159 |
| 2,7-Dimethyl Octane | 153 | 160 |

TABLE A-continued

| Azeotroping Agent | Azeotrope b.p., ° C 760 mm.Hg | Agent b.p., ° C 760 mm.Hg |
|---|---|---|
| p-Chlorotoluene | 155 | 162 |
| Mesitylene | 156 | 164.6 |
| 1,3-Dibromopropane | 160.2 | 167.3 |
| 2,6-Dimethyl-4-Heptanone | 164.2 | 168 |
| Pseudocumene | 158 | 169.5 |
| Phenetole | 161.5 | 172 |
| m-Dichlorobenzene | 166 | 172 |
| 2-Octanone | 168 | 172.9 |
| Benzylmethyl Ether | 159.8 | 174 |
| Decane | 161 | 174 |
| p-Dichlorobenzene | 163 | 174 |
| Hemimellitene | 163 | 176.1 |
| Heptyl Alcohol | 174.1 | 177 |
| p-Cymene | 163.2 | 177 |
| p-Methylanisole | 166.6 | 177 |
| bis-(2-chloroethyl) Ether | 171 | 178 |
| o-Dichlorobenzene | 165.8 | 179 |
| n-Butyl Benzene | 166.2 | 183.1 |
| 1,2-Diethylbenzene | 168 | 183.4 |
| Benzyl ethyl Ether | 169 | 185 |
| Amyl Ether | 168.8 | 187.5 |
| Phenyl propyl Ether | 171 | 190.2 |
| p-Tert.-Butyl Toluene | 173 | 193 |
| Durene | 174 | 194 |
| n-Octyl Alcohol | 184 | 195.2 |
| Isodurene | 175 | 197 |
| Acetophenone | 186 | 202 |
| Prehnitene | 176 | 204 |
| Benzyl Alcohol | 193 | 205 |
| Tetralin | 178 | 207.2 |
| Dodecane | 179 | 214.5 |
| Benzyl Acetate | 186.5 | 214.9 |
| 1,3,5-Triethyl Benzene | 183 | 215.4 |

As indicated above, the separation process of the invention is applicable to the recovery of ethylene glycol from mixtures of this compound with ethylene glycol lower carboxylate esters produced in any manner, but it is of particular utility in the separation of ethylene glycol from such mixtures produced by the azeotropic distillation of the character above described which distillation is preferably fed with mixtures produced by the hydrolysis of mono-and/or dicarboxylate esters of ethylene glycol and the azeotropic distillation can be readily integrated with the hydrolysis operation. The ethylene glycol-ester feed which is fed to the azeotropic distillation operation is a mixture of ethylene glycol with lower carboxylate mono-esters and/or diesters of ethylene glycol, i.e., esters of ethylene glycol and an alkanoic acid having from 1 to 6 carbon atoms per molecule, such as formic acid, acetic acid, propionic acid, butyric acid, isobutyric acid, and the valeric and the caproic acids. Accordingly, the lower carboxylate esters of ethylene glycol include ethylene glycol monoformate, ethylene glycol monoacetate, ethylene glycol monopropionate, ethylene glycol monobutyrate, ethylene glycol monoisobutyrate, the ethylene glycol monovalerates and the ethylene glycol monocaproates, and the diesters include the corresponding diesters of the same alkanoic acids. Ethylene glycol admixed with the ethylene glycol monoformate, ethylene glycol monoacetate, monopropionate, monobutyrate and monoisobutyrate, the corresponding diesters, and mixtures of such monoesters and such diesters, are typical feedstocks and the diacetatemonoacetate mixtures are particularly typical feedstocks. Of course, the ethylene glycol to be separated can also be present in mixtures of esters such as mixtures of ethylene glycol monoacetate and ethylene glycol monopropionate, as well as mixtures with one or more diesters, including mixed diesters such as ethylene glycol acetate propionate. The feed to the azeotropic distillation, therefore, is intended to include not only mixtures of ethylene glycol with the lower carboxylate ethylene glycol monoester alone or the ethylene glycol diester alone but also mixtures with monoester-diester mixtures or with mixed esters, as well as with mixtures of different ethylene glycol carboxylate esters. In general, mixtures containing the ethylene glycol may contain small amounts of by-products associated with the preparation of the glycol ester. Such by-products would normally include small quantities of water and acids and may also include catalyst residues and aldehydic by-products, such as, for example, acetaldehyde and formaldehyde. The azeotropic distillation is particularly applicable to ethylene glycol-ester mixtures containing 5 to 95 mol % of ethylene glycol.

Typically, the glycol-containing phase from the azeotropic distillation will be substantially free from the glycol diesters contained in the feed to the azeotropic distillation but glycol monoesters will be present since, although undergoing substantial separation in the azeotropic distillation, they tend to pass in part into the overhead and this is particularly true of acetates and formates, especially the formates. In a typical case in which the feed to the distillation of this invention is the ethylene glycol-containing phase obtained by the azeotropic distillation of a mixture of ethylene glycol and ethylene glycol esters derived from an ethylene glycol ester hydrolyzate, the feed to the azeotropic distillation column contains ethylene glycol and ethylene glycol monoesters in the ratio of about 0.1 to 1 mol of ethylene glycol to 1 mol of ester and the ethylene glycol-containing phase contains ethylene glycol in the ratio of 1.4 to 16 mols of ethylene glycol to 1 mol of monoester. Thus the further fractional distillation, however, effectively removes these monoesters and makes possible the ready recovery as a bottoms product of substantially pure ethylene glycol. This distillation is carried out under appropriate distillation conditions, most suitably at pot or reboiler temperatures of 120° to 210° C and pressures of 50 mm.Hg to 7 psig. Any azeotropic agent present in the overhead from this last-mentioned distillation step will generally phase separate and is advantageously recycled by combining it with the feed to the azeotropic distillation column. The glycol-ester phase can be recycled to the hydrolysis step when the azeotropic distillation of the invention is integrated with the hydrolysis of glycol esters.

As previously mentioned, the ethylene glycol-ester feed to the azeotropic distillation can comprise the effluent from the hydrolysis of ethylene glycol carboxylate esters, suitably after removal of water and carboxylic acid which effluent will contain not only the ethylene glycol monoester and generally the ethylene glycol diester but will also contain varying amounts of ethylene glycol. Thus, the reaction mixture from which the ethylene glycol is to be separated can be prepared by partially hydrolyzing mono- or di- carboxylate esters of ethylene glycol, or mixtures of said esters, by heating the ester or esters in the presence of water. Although the hydrolysis reaction will take place solely under the influence of heat, it may be preferred, in order to increase the rate of reaction, to effect hydrolysis in the presence of an acidic hydrolysis catalyst.

The feed to the hydrolysis operation can consist essentially of the monoester, or of the diester, or of mixtures of mono- or diesters in any proportion. The effluent from reactions which produce ethylene glycol monoester or ethylene glycol diester, or mixtures of the two, can be fed to the hydrolysis reaction. Typical reaction effluents of this nature are described, for example, in the above-mentioned Belgian Patent 738,104, wherein the monoester is produced in the presence of substantial quantities of the diester, and in British Patent No. 1,124,862, wherein the production of monoester substantially free from diester is disclosed. The hydrolysis step can be applied to glycol esters produced in any manner, whether by the process of the Belgian patent or the British patent or by various other processes. The hydrolysis reactions, regardless of the exact composition of the feed, continue until an equilibrium mixture comprising diester, monoester, ethylene glycol, carboxylic acid and water is formed. Before feeding the hydrolysis reaction product to the azeotropic distillation, the water and carboxylic acid are preferably removed from the hydrolysis effluent, e.g., by distillation in any convenient manner, these two compounds being readily separated from the ethylene glycol and the lower carboxylate esters. In effecting the hydrolysis, the ethylene glycol lower carboxylate ester, or ester mixture, is suitably heated in the presence of water until at least some hydrolysis has occurred. Although the hydrolysis reaction will take place solely under the influence of heat, it may be preferred, in order to increase the rate of reaction, to effect hydrolysis in the presence of small amounts of an acidic hydrolysis catalyst such as a mineral acid, e.g., sulphuric acid and phosphoric acid, but most preferably a solid catalyst, e.g., in the form of an acidic ion exchange resin, is employed, as described in the previously-mentioned Golden U.S. Pat. No. 3,809,724. The hydrolysis step is thus suitably carried out by causing the glycol ester or ester mixture to react under the influence of heat (with or without a catalyst) to liberate (i.e., hydrolyze) from 15 to 80 mol % of the acyl moieties. e.g., acetate moieties, as lower carboxylate acid, e.g., acetic acid, desirably using at least 0.25 mol of water, preferably 0.75 to 5 mols of water, per equivalent of acyl moiety present in the hydrolysis feed. In the course of the hydrolysis, ethylene glycol is liberated.

Hydrolysis reaction temperatures of at least about 50° C are generally used but, when catalysts are employed, temperatures as low as 25° C can be satisfactorily used. It is generally not desirable to employ hydrolysis reaction temperatures above about 250° C. Preferably, temperatures of about 50° C to about 200° C are employed. Pressure is not critical as long as it is sufficient at the prevailing temperature to keep the reaction mixture in the liquid phase. Thus, pressures of as little as 50 mm.Hg can be employed as also can pressures of several thousand psia. Residence time of reactants and products within the hydrolysis zone is not critical. Thus, for example, residence times from as little as 1 minute up to and including several hours, e.g., 4 hours, or longer are entirely feasible.

Following the hydrolysis reaction, the hydrolyzate, which contains carboxylic acid, e.g., acetic acid, and water, in addition to ethylene glycol, monoesters, and diesters, is, as mentioned, suitably passed into a distillation column wherein a major portion of the carboxylic acid and water is vaporized and removed as overhead for subsequent recovery. This separation can be carried out in any conventional distillation column, such as used for the azeotropic distillation. In general, it is desirable to separate at least 90% of the water and carboxylic acid present in the mixture before proceeding with the removal and recovery of the ethylene glycol by azeotropic distillation. Although the distillation step to separate water and carboxylic acid can be carried out over a wide range of conditions, it has been found preferable to operate at pot or reboiler temperatures of 170° to 240° C and at pressures of from 400 mm.Hg to 50 psig. It will be understood that the water and carboxylic acid can be removed in a single distillation operation or the distillation may be carried out in two distillation zones in series with the water and some of the carboxylic acid being removed in the first distillation zone and the remainder of the carboxylic acid to be removed being separated in the second distillation zone. The distillation can be carried out in conventional manner and the selection of specific conditions for treatment of specific feeds will be readily apparent to persons skilled in the art. The above-described hydrolysis and preliminary distillation are suitably carried out in the manner discussed and exemplified in Golden U.S. Pat. No. 3,809,724.

Referring again to the azeotropic distillation operation, the distillation unit in which the azeotropic distillation is carried out can be any convenient fractional distillation unit, e.g., a plate column or a packed column, having a sufficient number of theoretical plates for the desired separation, generally, from 15 to 50 theoretical plates. The temperature will, of course, vary with the particular azeotroping agent, since each agent forms a minimum-boiling binary azeotrope with ethylene glycol having a different boiling point but, in general, pot temperatures off 170° to 250° C are employed in the distillation. Similarly, pressures of from 400mm.Hg to 50 psig are suitably employed. The azeotrope, when condensed, separates into a first phase, generally the upper phase, composed primarily of ethylene glycol; this ethylene glycol phase contains a small amount of ethylene glycol monocarboxylate ester which, when present in the system, will tend to distill with the azeotropic mixture to a greater or lesser extent depending on the azeotroping agent employed. The vapor condensate from the azeotropic distillation operation is therefore passed to a separator or decanter and the azeotroping agent-containing phase is returned as reflux to the distillation column. It will be understood, however, that operation outside the above-mentioned temperature and pressure ranges is possible and, the specific choice of specific combinations of conditions is entirely within the scope of persons skilled in the art.

Ethylene glycol is recovered from the ethylene glycol phase in accordance with the invention by distillation. Thus, the ethylene glycol-containing phase from the azeotropic condensate is subjected to further distillation to remove an overhead comprising ethylene glycol monocarboxylate ester present in the feed along with a relatively small amount of ethylene glycol, together with any azeotroping agent which may be present, and pure ethylene glycol is withdrawn as bottoms product. The glycol-ester phase of the overhead product from this last-mentioned distillation step which will contain the acetic and/or formic acid is advantageously recycled to the system, preferably to the esterhydrolysis step. This distillation is carried out under appropriate distillation conditions, preferably at temperatures of 150° to 210° C, and pressures of 150 mm.Hg to 5 psig. As in the case of the azeotropic distillation column, the fractional distillation of the present invention is suitably carried out in any conventional fractional distillation unit, e.g., a plate column or a packed column, having a sufficient number of theoretical plates for the desired separation, generally from 20 to 40 theoretical plates. The distillation column is suitably provided with the usual still or reboiler to provide the necessary distillation heat. The particular distillation means forms no part of the present invention and the selection of appropriate distillation equipment will be readily apparent to persons skilled in the art. As indicated above, the feed to the fractional distillation of the invention, typically from the azeotropic distillation of a glycol-lower carboxylate ester mixture derived from the hydrolysis of lower carboxylate esters, and containing up to 65 mol % of glycol monoester is continuously fed into the central portion of the fractional distillation column, the term "central portion" being used to mean the portion of the column lying between its lower third and its upper fourth sections, and the feed is continuously distilled to remove an overhead distillate containing the ethylene glycol monoester along with some ethylene glycol and any azeotropic agent which may be present in the feed. At the same time, there is fed into the distillation column at a point below the point of introduction of the feed a supply of aqueous formic acid and/or acetic acid to bring about the suppression of the formation of the previously described conversion product of the glycol monoester, referred to as the corresponding ortho ester. While the aqueous formic acid and/or acetic acid additive can be introduced at any point below the feed point to the column, it is preferably introduced at a point which is 1–5 theoretical trays above the reboiler or pot. As previously mentioned, a small amount of water is added to the pot or reboiler.

The product withdrawn as bottoms from the distillation column will be highly purified with respect to the glycol monoester and azeotropic agent which may be present in the feed to the distillation. However, there may be present in the purified glycol thus recovered as bottoms a very small proportion of higher boiling materials such as di-ethylene glycol and like condensation products which sometimes form. In order, therefore, to remove such higher boiling materials, the product ethylene glycol is preferably submitted to a final fractional distillation in which the ethylene glycol is distilled away from any higher boiling materials and is recovered as a purified distillate product. This final distillation is a conventional fractional distillation, typically carried out in a column containing 10 to 20 theoretical plates operated at a pressure of 50 to 600 mm. with a pot temperature of 120° to 190° C.

Figure 2:
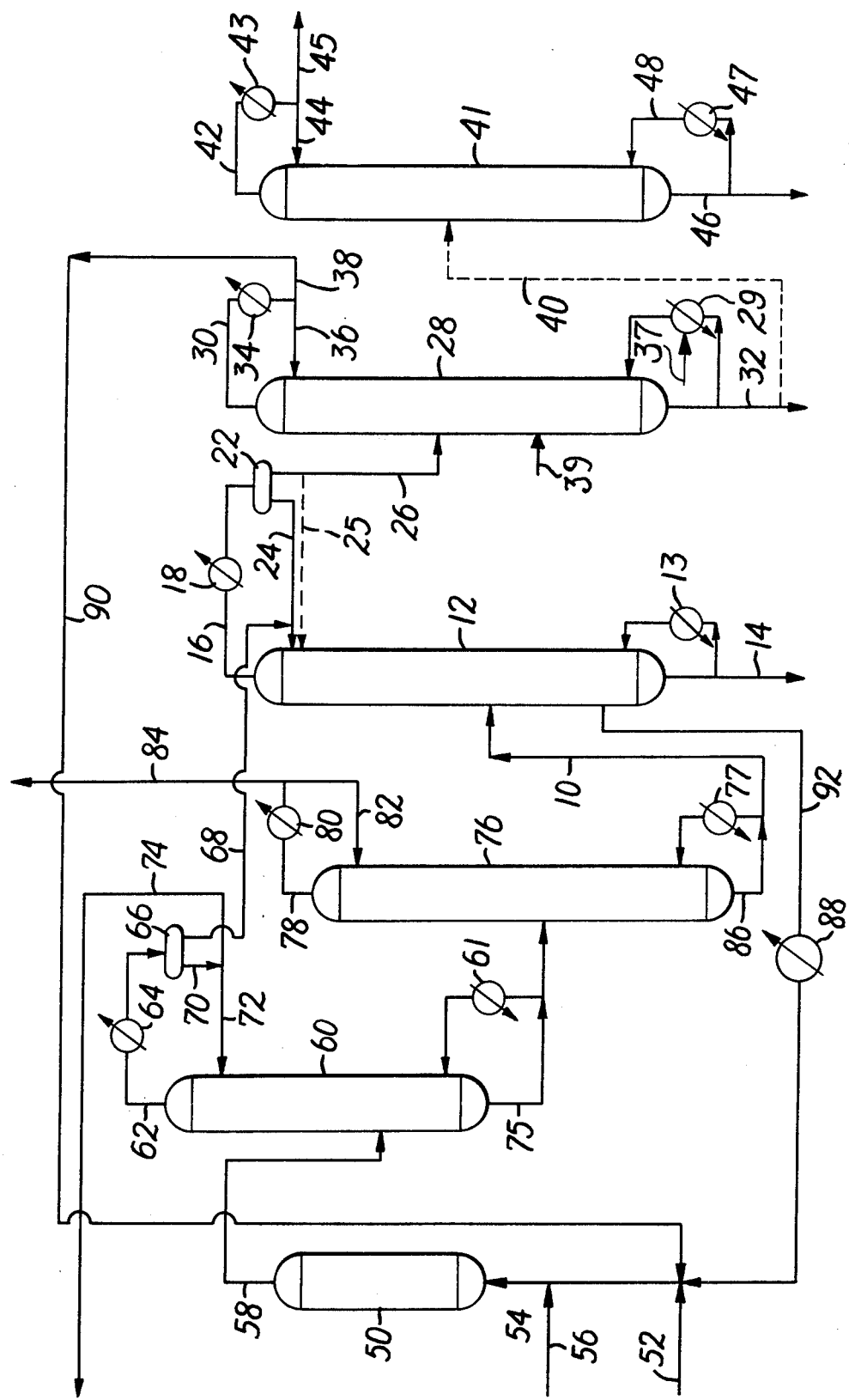

The invention will be more fully understood by reference to the accompanying drawing, wherein:

FIG. 1 is a diagrammatic view of an ethylene glycol recovery system embodying the fractional distillation system of the invention, and FIG. 2 is a similar diagrammatic view of an overall system wherein the multiple distillation recovery system is integrated with an ethylene glycol ester hydrolysis.

Referring to the drawing, and more particularly to FIG. 1, an ester feed stream comprising an ethylene glycol ester mixture is fed through line 10 to azeotropic distillation zone 12, which in the embodiment illustrated, is a distillation column suitably provided with heating means, e.g., a convenient reboiler 13 and with a bottoms withdrawal line 14 and an overhead vapor line 16, the latter being connected to a condenser 18. The ethylene glycol is removed through line 16 in the form of an azeotrope with the azeotroping agent, and glycol ester is withdrawn through line 14. The overhead vapor from column 12 leaves through line 16 and is condensed in condenser 18, flows to a phase-separator 22, and the condensed azeotroping agent is returned to column 12 through line 24 as reflux, whereas the ethylene glycol phase is withdrawn through line 26 and is introduced into a refining column 28, also provided with a heating means, suitably in the form of a reboiler 29. A portion of the ethylene glycol phase may be returned to zone 12 as a reflux if desired as disclosed in the above-mentioned application of Chun Fei Chueh (Case 1088), the disclosure of which is incorporated herein by reference. In column 28, ethylene glycol ester and azeotroping agent contained in the ethylene glycol phase withdrawn from phase separator 22 is removed as vapor through line 30, and ethylene glycol in substantially purified form is withdrawn as bottoms through line 32. The vapors in line 30 are condensed in condenser 34 and a portion is returned as reflux to column 28 through line 35 and the remainder is withdrawn through line 38. Portions of the material in line 38 may, if desired, be combined with the feed to column 12, and make-up azeotroping agent, as required, may be added through line 10 or added to line 24. The introduction of water and acetic acid and/or formic acid into column 28 in accordance with the invention is indicated diagrammatically by line 39 and a line 37 is shown diagrammatically for the optional introduction of water to reboiler 29. As previously mentioned, the purified ethylene glycol withdrawn through line 32 is preferably given a final distillation to insure against the presence in the product of higher boiling materials such as diethylene glycol and the like. Thus, ethylene glycol from line 32 is passed through line 40 into distillation column 41 to remove purified glycol through line 42 leading to a condenser 43, the condensate from which is partially returned to column 41 as reflux through line 44, and the remainder is withdrawn as product glycol through line 45. The heavier components separated by the distillation are removed through line 46. The reboiler 47 in line 48 provides the necessary heat for maintenance of the distillation.

Referring now to FIG. 2, wherein the azeotropic distillation system just described is integrated with the hydrolysis of lower carboxylate esters of ethylene glycol to provide the feed to azeotropic distillation column 12, a hydrolysis ester feed stream enters a hydrolysis zone 50 through line 52 and line 54 and water for the hydrolysis enters through line 56 and is combined with the hydrolysis ester feed in line 54 before entering zone 50. Zone 50 is suitably filled with a bed of solid hydrolysis catalyst, e.g., a bed of acidic ion exchange resin and the combined water and ester feed stream flows upwardly through the bed and the hydrolyzed reaction product is removed through line 58. The product stream in line 58 is introduced into a water separation column 60, provided with a reboiler 61 or other heating means. In column 60, water is vaporized and, along with a small amount of carboxylic acid, is withdrawn through line 62 and condensed in condenser 64. Since, in the embodiment illustrated in FIG. 2, the condensate from condenser 64 will contain some azeotroping agent, as will be explained below, the condensate passes to a phase separator 66 wherein the water and carboxylic acid form one phase and the azeotroping agent forms a second phase, the latter being withdrawn from separator 66 through line 68. The aqueous phase is withdrawn through line 70, with part of it being returned to column 60 through line 72 as reflux and the remainder being recycled to reactor 50 through line 74 which empties into water supply 56. The portion of the hydrolysis product stream supplied to column 60 which is not vaporized and withdrawn through line 62 and which comprises ethylene glycol, carboxylic acid and lower carboxylate esters of ethylene glycol is withdrawn through line 75 and fed to a distillation column 76, also provided with appropriate heating means, e.g., a reboiler 77. In distillation column 76, the carboxylic acid is vaporized and carboxylic acid vapors are withdrawn through line 78 and condensed in condenser 80 with some of the condensate being returned to column 76 as reflux through line 82 and the remainder being withdrawn from the system through line 84. The carboxylic acid stream will also contain any water which was not separated in column 60. The essentially water- and carboxylic acid-free ethylene glycol-lower carboxylate ester mixture is withdrawn from distillation zone 76 through line 86 and is supplied to line 10 to provide the ester feed to azeotropic distillation zone 12, as described above in connection with the discussion of FIG. 1. To complete the integration of the azeotropic distillation system with the hydrolysis system, a line 90 connects with line 38 to conduct the withdrawn condensate containing azeotroping agent from column 28 to the feed to hydrolysis zone 50 and a side stream from column 12 comprising vapors of lower carboxylate esters of ethylene glycol is withdrawn through line 92 and also combined with the feed of the hydrolysis zone, after being condensed by condenser 88.

The following examples of specific application will serve to give a fuller understanding of the invention but it will be understood that these examples are illustrative only and are not intended as limiting the invention.

A mixture containing 34.6 mol% ethylene glycol, 42.2 mol % ethylene glycol monoacetate, 12.8 mol % ethylene glycol diacetate, 7.9 mol % ethylene glycol monoformate and 2.5 mol % ethylene glycol acetate formate was azeotropically distilled in the presence of 1,2,3-trimethylbenzene as an azeotroping agent with a pot temperature of 230° C under a pressure of 30 psig to produce a purified overhead ethylene glycol stream containing 14.5 mol % monoester and 2 mol % of the azeotroping agent. Several portions of this product were then continuously fractionally distilled at a feed rate of 1 kg/hr. for 48 hours in a 2 inches diameter distillation column containing 40 theoretical plates (18 theoretical plates above the feed point and 22 theoretical plates below the feed point) and provided with the usual reboiler and overhead condenser. Distillation was carried out at a pressure of about 150 mm.Hg with a bottoms or reboiler temperature of about 170° C and an overhead temperature of about 125° C, using a reflux ratio of 2.3:1. During the distillation, several tests were carried out to demonstrate the effect of the addition of small amounts of water, acetic acid and/or formic acid, these additives being added at a point in the column below the feed point corresponding to 5 theoretical trays above the reboiler. These distillations are described in Examples 1 to 5 below.

EXAMPLE 1

In this experiment, no water, no acetic acid and no formic acid were added to the distillation column, the operation being simply a fractional distillation of the feed without the introduction of any additives. The purified glycol removed as bottoms from the distillation was analyzed and found to contain 30 ppm of monoester, approximately 500 ppm of diethylene glycol, a trace of diethylene glycol ester, and 6,550 ppm of ortho ester.

EXAMPLE 2

In this experiment, 2 wt. % (based on the feed) of water was added and analysis of the ethylene glycol bottoms product showed it to contain about 30 ppm of ethylene glycol monoester, about 500 ppm of diethylene glycol, a trace of diethylene glycol ester, and 1,240 ppm of ortho ester.

EXAMPLE 3

The experiment of Example 1 was repeated, except that there was also added 1 wt. % acetic acid. The glycol product was similar to that of Example 2, except that the ortho ester had been reduced to 360 ppm.

EXAMPLE 4

The experiment of Example 2 was again repeated, except that there was also added 1 wt. % of formic acid. The glycol bottoms product showed a content of 50 ppm of ethylene glycol monoacetate, 800 ppm of diethylene glycol, 60 ppm of diethylene glycol ester, but only 65 ppm of ortho ester.

EXAMPLE 5

In this experiment, the additives to the distillation consisted of 2 wt. % water, 0.9 wt. % acetic acid and 0.1 wt. % formic acid. At the same time, 1 wt. % of water was added to the reboiler. Analysis of the glycol bottoms product showed it to contain 25 ppm ethylene glycol monoester, about 500 ppm of diethylene glycol, 60 ppm of diethylene glycol ester, and less than 20 ppm of ortho ester.

The bottoms products from the foregoing distillations are then suitably given a final distillation in a fractional distillation column containing 15 theoretical plates, operated at 170° C reboiler temperature and a pressure of 150 mm to separate pure glycol from the higher boiling components.

As previously mentioned, while the invention has been primarily described and illustrated with reference to the recovery of ethylene glycol, similar results are obtained when the ethylene glycol is replaced by propylene glycol. It will be understood, therefore, that all matter contained in the foregoing description and illustrated in the drawing is to be interpreted as illustrative only and not as limitative of the invention and various changes and modifications which will be apparent to those skilled in the art may be made without departing from the scope of the invention as defined in the appended claims.

We claim:
1. A process for purifying by distillation ethylene glycol or propylene glycol admixed with the lower alkanoate monoester of said glycol and an azeotroping agent originating from a previous distillation to produce a purified glycol substantially free from said azeotroping agent, said monoester and the corresponding ortho ester, which tends to form during said distillation which comprises introducing said glycol to be purified into a fractional distillation zone, introducing at least one of an aqueous acetic acid and an aqueous formic acid in said zone at a point below the point of introduction, into said zone of said glycol to be purified in an amount sufficient to substantially suppress the formation of said ortho ester and recovering purified glycol from the lower portion of said zone.

2. A process as defined in claim 1, wherein the amount of water contained in said aqueous acid is 0.5 to 10% by weight of the feed to said distillation zone, the amount of formic acid is 0.02 to 2.5% by weight of the feed to said distillation zone and the amount of acetic acid is 0.02 to 5% by weight of feed to said distillation zone.

3. A process as defined in claim 1, wherein both aqueous acetic acid and aqueous formic acid are introduced into said distillation zone.

4. A process as defined in claim 1, wherein the lower portion of said fractional distillation zone is connected to a reboiler zone and water is added to said reboiler zone.

5. A process as defined in claim 4, wherein the amount of water is 0.5 to 1.5% by weight of the feed to the distillation zone.

* * * * *